(12) United States Patent
Dumeunier et al.

(10) Patent No.: US 8,450,499 B2
(45) Date of Patent: May 28, 2013

(54) PROCESS FOR THE PREPARATION OF PYRAZOLE CARBOXYLIC ACID AMIDES

(75) Inventors: Raphael Dumeunier, Stein (CH); Hans Tobler, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/642,512

(22) PCT Filed: Apr. 14, 2011

(86) PCT No.: PCT/EP2011/055869
§ 371 (c)(1),
(2), (4) Date: Oct. 19, 2012

(87) PCT Pub. No.: WO2011/131543
PCT Pub. Date: Oct. 27, 2011

(65) Prior Publication Data
US 2013/0041161 A1 Feb. 14, 2013

(30) Foreign Application Priority Data
Apr. 20, 2010 (EP) ..................................... 10160440

(51) Int. Cl.
*C07D 231/10* (2006.01)
*C07D 303/02* (2006.01)
*C07C 211/43* (2006.01)

(52) U.S. Cl.
USPC .................... 548/374.1; 549/545; 564/428

(58) Field of Classification Search ............... 548/374.1; 549/545; 564/428
See application file for complete search history.

(56) References Cited

FOREIGN PATENT DOCUMENTS
WO 2007/048556 5/2007

OTHER PUBLICATIONS

Hiroshi Tanida et al: Journal of the American Chemical Society, vol. 86, No. 22, Nov. 20, 1964, pp. 4904-4912.
International Search Report, International Application No. PCT/EP2011/055869, completion date: Jun. 14, 2011.

*Primary Examiner* — Samantha Shterengarts
(74) *Attorney, Agent, or Firm* — R. Kody Jones

(57) ABSTRACT

The invention relates to a process for the preparation of formula (I), which process comprises a) reacting the compound (II), with cyclopentadiene to (III); b) reacting this compound in the presence of an oxidant to the compound of formula (IV); c) hydrogenating this compound in the presence of a metal catalyst and an inert solvent under hydrogen atmosphere to the compound of formula (V); d) reacting this compound in the presence of a Brönsted acid followed by a reducing agent to the compound of formula (VI); e) reacting VI with a compound (VII), in the presence of a base to a compound of formula (VIII); f) converting the compound of formula VIII in the presence of an oxidizing agent to the compound of formula (IX); and g) reacting the compound of formula IX in the presence of triphenylphosphane/carbon tetrachloride or riphenylphosphane/bromotrichloromethane to the compound of formula I.

11 Claims, No Drawings

PROCESS FOR THE PREPARATION OF PYRAZOLE CARBOXYLIC ACID AMIDES

This application is a 371 of International Application No. PCT/EP2011/055869 filed Apr. 14, 2011, which claims priority to EP 10160440.3 filed Apr. 20, 2010, the contents of which are incorporated herein by reference.

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described for example in WO 2007/048556.

The preparation of 3-difluoromethyl-1-methyl-1H-pyrazole-4-carboxylic acid (9-dichloromethylene-1,2,3,4-tetrahydro-1,4-methano-naphthalen-5-yl)-amide is known from WO 2007/048556. Said compound can be prepared according to schemes 1 and 4 by a) reacting the compound of formula A

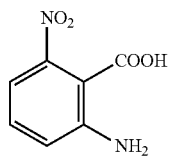

(A) in the presence of an alkyl nitrite with a compound of formula B

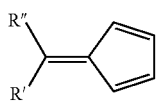

(B) wherein R' and R" are e.g. $C_1$-$C_4$alkyl, to a compound of formula C

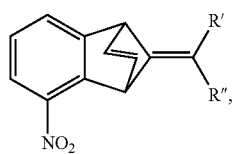

b) hydrogenating the compound of formula C in the presence of a suitable metal catalyst to a compound of formula D

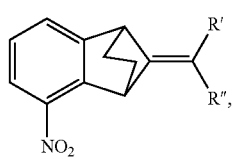

c) ozonising the compound of formula D and subsequent treatment with a reducing agent to a compound of formula E

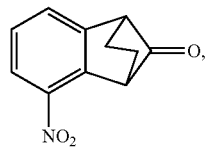

d) reacting the compound of formula E in the presence of triphenylphosphane/carbon tetrachloride to 2,9-dichloromethylidene-5-nitro-benzonorbornene of formula F

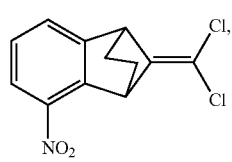

e) hydrogenating the compound of formula F in the presence of a metal catalyst to 2,9-dichloromethylidene-5-amino-benzonorbornene of formula G

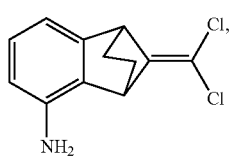

f) and reacting the compound of formula G with a compound of formula H

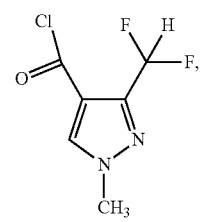

to 3-difluoromethyl-1-methyl-1H-pyrazole-4-carboxylic acid (9-dichloromethylene-1,2,3,4-tetrahydro-1,4-methano-naphthalen-5-yl)-amide.

A significant disadvantage of this prior art process is the ozonolysis reaction which is difficult to handle. Said disadvantage makes this process uneconomical and especially unsuitable for a large-scale production.

The aim of the present invention is therefore to provide a novel process for the production of 3-difluoromethyl-1-methyl-1H-pyrazole-4-carboxylic acid (9-dichloromethylene-1,2,3,4-tetrahydro-1,4-methano-naphthalen-5-yl)-amide that avoids the disadvantages of the known process and makes it possible to prepare 3-difluoromethyl-1-methyl-1H-pyrazole-4-carboxylic acid (9-dichloromethylene-1,2,3,4-tetrahydro-1,4-methano-naphthalen-5-yl)-amide in high yields and good quality in an economically advantageous way.

Thus, according to the present invention, there is provided a process for the preparation of the compound of formula I

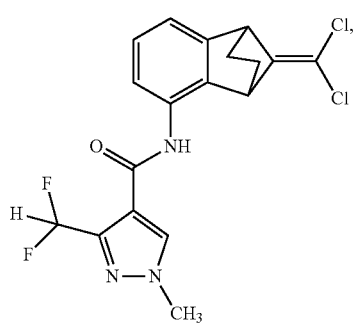
(I)

which process comprises a) reacting the compound of formula II

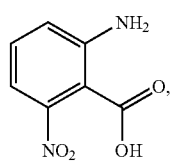
(II)

with cyclopentadiene in the presence of an alkylnitrite and an inert solvent to a compound of formula III

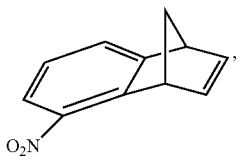
(III)

b) reacting the compound of formula III in the presence of an oxidant and an inert solvent to the compound of formula IV

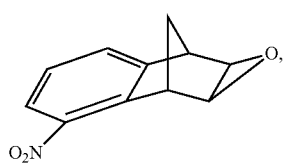
(IV)

c) hydrogenating the compound of formula IV in the presence of a metal catalyst and an inert solvent under hydrogen atmosphere to the compound of formula V

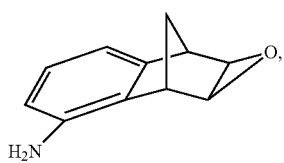
(V)

d) reacting the compound of formula V in the presence of a Brönsted acid followed by a reducing agent to the compound of formula VI

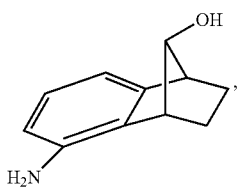
(VI)

e) reacting the compound of formula VI with a compound of formula VII (VII)

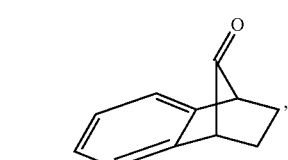

in the presence of a base to a compound of formula VIII (VIII)

f) converting the compound of formula VIII in the presence of an oxidising agent to the compound of formula IX (IX)

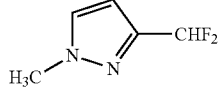

and g) reacting the compound of formula IX in the presence of triphenylphosphane/carbon tetrachloride or triphenylphosphane/bromotrichloromethane to the compound of formula I.

The use of cyclopentadiene in the cycloaddition step of the process of this invention is very advantageous since the use of cyclopentadiene gives generally better yields than fulvenes, such as dichlorofulvene or dimethylfulvene, used in the process described in WO 2007/048556. It is also directly available from the commercially available dimer.

Reaction Step a):

The reaction is preferably performed at slightly elevated temperatures, in particular from 40 to 60° C. The preferred temperature is at reflux of the solvent, when it does not exceed 60° C. Suitable inert solvents for this reaction step are chlorinated alkanes, such as chloroform or dichloroethane, with a preference for dichloromethane; ethers such as dimethoxyethane or THF; ketones such as acetone or methylethylketone, with a preference for methylethylketone; or esters such as methylacetate or ethyacetate, with a preference for the latter.

Preferred alkyl nitrites are n-butylnitrite, tert- or isoamylnitrite, in particular isoamylnitrite or tert-butylnitrite. The compound of formula II is known in the art and can be prepared, for example according to WO 2007/031323 from 3-nitro-phthalimide which can be converted by reaction with an aqueous base, and by subsequent reaction with an aqueous acid into 6-nitrophthalamic acid. The 6-nitrophthalamic acid may be reacted first with an aqueous base, such as, for example, aqueous sodium hydroxide, and sodium hypochlorite, and then with aqueous acid, such as, for example, aqueous hydrochloric acid to obtain the compound of formula II.

Reaction Step b):

Suitable oxidants are performic acid, peracetic acid or hydrogen peroxide in combination with an organic acid such as acetic acid. Carbamide peroxide in the presence of disodium hydrogen phosphate and acetic anhydride is also a suitable system for this oxidation. A preferred oxidant is meta-chloro-perbenzoic acid. Suitable solvents for reaction step b) are for example chloroform, acetonitrile, tetrahydrofurane, dichloromethane, dimethoxyethane or dioxane. Dichloromethane is preferred. The reaction can be performed at a temperature from 0° C. to the refluxing temperature of the solvent, preferably at 20-30° C. The compound of formula IV is novel, is especially developed for the process according to the invention and therefore constitutes a further object of the invention.

Reaction Step c):

Suitable metal catalysts are Palladium, Platinum or Rhodium on Carbon, or Raney Nickel. The preferred catalyst is Rhodium on Carbon.

The reaction can be ran under hydrogen pressure or under normal atmospheric pressure, with a temperature ranging from ambient to the refluxing temperature of the solvents. Suitable solvents are for example tetrahydrofuran ethyl acetate, dioxane or ethanol, preferably tetrahydrofuran.

In a preferred variant of reaction step c) tetrahydrofuran is used as the solvent and the reaction is performed at ambient temperature and atmospheric pressure of hydrogen, combined with the use of a dry rhodium on carbon heterogeneous catalyst.

The compound of formula V is novel, is especially developed for the process according to the invention and therefore constitutes a further object of the invention.

Reaction Step d):

Having a biphasic system in the first part of the reaction is preferred. Useful solvents for the organic phase are alkanes. Heptane is preferred. Hydrobromic acid in water is the preferred Brönsted acid to perform the rearrangement. The reaction can be performed at temperatures between 5° C. and 40° C., with a preference for 20° C.

For the second part of the transformation, suitable reducing agents such as Fe/HCl, Zn/HCl or Zn/AcOH may be used. Preferred is the combination of activated zinc and acetic acid. Preferred solvents for the reduction are alcohols, for example methanol and ethanol, the preferred being methanol. The reaction is performed at a temperature from 0° C. to the reflux temperature of the solvent, preferably at 20° C.

The compound of formula VI is novel, is especially developed for the process according to the invention and therefore constitutes a further object of the invention.

Reaction Step e):

Coupling reactions between an amine and an acyl chloride are generally known. The presence of a base, usually tertiary amines such as diisopropylethylamine or triethylamine, but also amines such as pyridine or 2,6-lutidine or NaOH, preferably tertiary amines, is beneficial to quench the hydrochloric acid formed during the reaction.

Lewis base catalysts may also be used to accelerate the reaction, the archetypal catalyst for such a transformation being 4-dimethylamino-pyridine.

Inerts solvents such as chloroform, dichloroethane, dichloromethane; ethers such as dimethoxyethane, tetrahydrofurane, dioxane, toluene, chlorobenzene or xylene are suitable for this reaction step.

The temperature might range from 0° C. to the reflux of the solvent.

Preferred reaction conditions are the presence of triethylamine as a base, the absence of a catalyst and dichloromethane as a solvent, at ambient temperature.

The compound of formula VII is known and is disclosed, for example, in U.S. Pat. No. 5,093,347. The compound of formula VIII is novel, is especially developed for the process according to the invention and therefore constitutes a further object of the invention.

Reaction Step f):

Methods to oxidise a secondary alcohol to a ketone are described in the prior art, most of them would be suited for this particular transformation.

The mild Swern oxidation is a chemical reaction whereby a primary or secondary alcohol is oxidized to an aldehyde or ketone using oxalyl chloride, dimethyl sulfoxide and an organic base, such as triethylamine. It can be performed in inert solvents such as chlorinated alkanes, and the temperature has to be maintained preferably between −78° C. and −55° C. before the final addition of the base.

g) The conversion can be performed in the presence of for example triphenylphosphane/carbontetrachloride or triphenylphosphane/bromotrichloromethane. A preferred solvent is acetonitrile, the temperature might range from 0° C. to 60° C., with a preference for 60° C. This reaction step is also described in PCT/EP2009/067286.

PREPARATORY EXAMPLES

Step a): Preparation of the Compound of Formula III

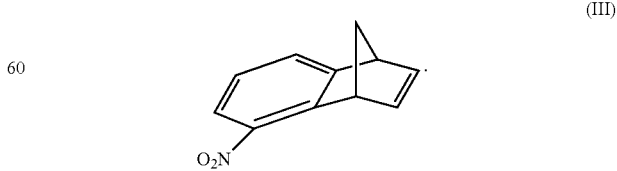

In a three necked flask equipped with thermometer, dropping funnel and cooler with a bubbler, tertio-butyl nitrite (5.77 ml, 1.77 eq, 48.6 mmol) is dissolved in dichloromethane (30 ml) and heated to reflux while a solution of cold 2-amino-6-nitro-benzoic acid (5 g, 1 eq, 27.5 mmol) and cyclopentadiene (40.7 ml, 18 eq, 0.49 mol) in acetone (20 ml) is added dropwise. Care should be taken regarding gas evolution. After refluxing for 18 hours, the reaction is cooled down to ambient temperature before being filtrated through a silica pad and evaporated. The crude mixture is purified by chromatography column (silica gel, elution with a gradient from pure cyclohexane to a mixture of ethyl acetate:cyclohexane 1:12. 3 grams of 5-nitro-1,4-dihydro-1,4-methano-naphthalene are then obtained (58% yield). $^1$H NMR (CDCl$_3$) 7.7 ppm, 1H, dd, J=0.7 and 8.4 Hz; 7.45 ppm, 1H, dt, J=7.3 and 0.7 Hz; 7.07 ppm, 1H, dd, J=7.3 and 8.4 Hz; 6.9-6.86 ppm, 2H, m; 4.86 ppm, 1H, bs; 4.02 ppm, 1H, bs; 2.38 ppm, 1H, dt, J=7.7 and 1.5 Hz; 2.3 ppm, 1H, dt, J=7.4 and 1.5 Hz.

Step b) Preparation of the Compound of Formula IV:

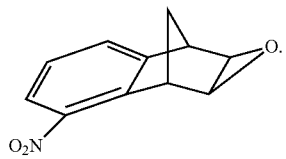

(IV)

To a solution of meta-chloro-perbenzoic acid (2.12 g, 1.08 eq, 9.23 mmol) in dichloromethane (12.8 ml) stirred at ambient temperature is added a solution of 5-nitro-1,4-dihydro-1,4-methano-naphthalene (1.6 g, 1 eq, 8.55 mmol) in dichloromethane (20.5 ml). After stirring for 1 hour, the excess of meta-chloro-perbenzoic acid is destroyed by the addition of an aqueous sodium sulphite solution, and the organic layer is washed successively with a saturated aqueous sodium bicarbonate solution and water. It is then dried over solid sodium sulphate, concentrated under vacuum and the residue is purified by chromatography column (silica gel, elution with cyclohexane:ethyl acetate 6:1). 1.55 g of the title compound is obtained (89% Yield). $^1$H NMR (CDCl$_3$) 7.84 ppm, 1H, dd, J=1.1 and 8.4 Hz; 7.50 ppm, 1H, dd, J=0.7 and 7.3 Hz; 7.23 ppm, 1H, dd, J=7.1 and 8.4 Hz; 4.38 ppm, 1H, bs; 3.56 ppm, 1H, bd, J=3.7 Hz; 3.54 ppm, 1H, bs; 3.44 ppm, 1H, bd, J=3.7 Hz; 2.03 ppm, 1H, dt, J=9.5 and 1.5 Hz; 1.6 ppm, 1H, bd, J=9.5 Hz.

Step c): Preparation of the Compound of Formula V

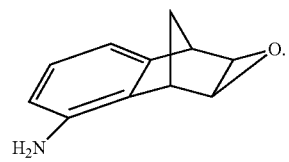

(V)

To a solution of the compound of formula IV (product of step b) (200 mg, 1 eq, 0.98 mmol) in tetrahydrofuran (6 ml) is added rhodium on carbon (5 wt. %, 83 mg). The atmosphere is changed to argon, then to hydrogen, and the reaction mixture is stirred at ambient temperature for 5 hours. The atmosphere is changed back to argon, before filtering the mixture over celite. The solvent is removed under vacuum and the residue (166 mg, 97% Yield) is used directly in the next step without purification. $^1$H NMR (CDCl$_3$) 6.89 ppm, 1H, dd, J=7.3 and 8.1 Hz; 6.74 ppm, 1H, d, J=7.1 Hz; 6.48 ppm, 1H, d, J=8.1 Hz; 3.44 ppm, 1H, s; 3.43 ppm, 1H, m; 3.40 ppm, 1H, m; 3.38 ppm, 1H, s; 1.95 ppm, 1H, bd, J=8.8 Hz; 1.52 ppm, 1H, bd, J=8.8 Hz.

Step d) Preparation of the Compound of Formula VI

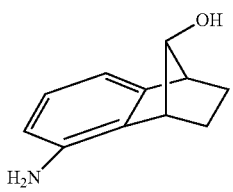

(VI)

d1) To a solution of the compound of formula V (product of step c) (0.9 g, 1 eq, 5.19 mmol) in heptane (9 ml) is added hydrobromic acid (48% aqueous, 1.23 ml, 2.1 eq, 10.9 mmol). The resulting mixture is stirred at ambient temperature for 2 hours, before being diluted with ethyl acetate and neutralised with saturated aqueous sodium bicarbonate solution. The aqueous layer is extracted twice with ethyl acetate, the combined organic phases are washed successively with a saturated aqueous sodium bicarbonate solution and brine. The organic phase is then dried over solid sodium sulphate, filtrated and concentrated under vacuum. The residue is composed of two isomers, the structures of which are disclosed hereafter.

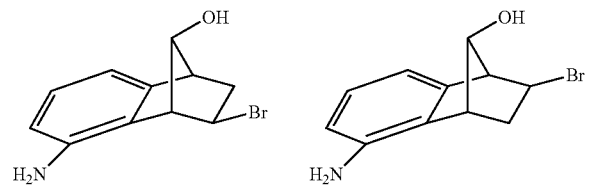

d2) 960 mg (73% of theory) of this residue are dissolved in methanol (14 ml); zinc powder (1.85 g, 7.5 eq, 28.3 mmol) and acetic acid (0.93 ml, 4.3 eq, 16.24 mmol) are then added successively. The mixture is then stirred 2 hours at ambient temperature, before being diluted with ethyl acetate and filtered over celite. The filtrate is evaporated, and the crude is dissolved in a mixture of dichloromethane:methanol. Isolute HM-N (diatomaceous earth) is added, solvents are removed, and the remaining solid is loaded, dry, on a silica gel choromatography column. It is then eluted first with a 2:1 mixture of ethyl acetate:heptane, then with ethyl acetate pure. 363 mg of 5-amino-1,2,3,4-tetrahydro-1,4-methano-naphthalen-9-ol of formula VI are then obtained (40% Yield). $^1$H NMR (CDCl$_3$) 6.95 ppm, 1H, dd, J=7.3 and 8.1 Hz; 6.65 ppm, 1H, d, J=7.3 Hz; 6.51 ppm, 1H, dd, J=0.7 and 8.1 Hz; 3.82 ppm, 1H, bs; 3.1-3.08 ppm, 2H, m; 2.1 ppm, 2H, dd, J=2.9 and 9.9 Hz; 1.2 ppm, 2H, m.

Step e): Preparation of the Compound of Formula VIII

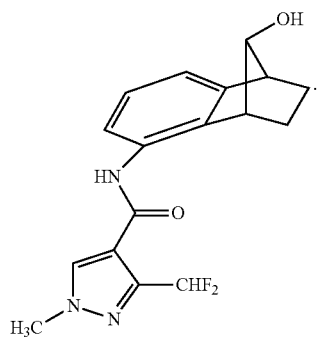 [SMILES: Cn1cc(C(=O)Nc2cccc3c2C2CCC3C2O)c(C(F)F)n1]

(VIII)

To a solution of 5-amino-1,2,3,4-tetrahydro-1,4-methano-naphthalen-9-ol (61 mg, 0.35 mmol, 1 eq) in dichloromethane (1.2 ml) is added successively at a temperature of 0° C. ethyl-diisopropyl-amine (0.12 ml, 0.7 mmol, 2 eq) and 3-difluoromethyl-1-methyl-1H-pyrazole-4-carbonyl chloride of formula VII (61 mg, 0.31 mmol, 0.9 eq). The reaction mixture is stirred one hour at 0° C. and 16 hours at ambient temperature, before being diluted with ethyl acetate and poured on water. After separation of the layers, the aqueous phase is extracted twice with ethyl acetate, the combined organic extracts are washed twice with a saturated aqueous sodium bicarbonate solution, before being dried over solid sodium sulphate, filtered and concentrated under vacuum. The residue is purified by chromatography column (silica gel, elution with dichloromethane:methanol 39:1). 67 mg of the title compound are obtained (58% Yield). $^1$H NMR (CDCl$_3$) 8.14 ppm, 1H, bs; 8.01 ppm, 1H, s; 7.83 ppm, 1H, d, J=8.1 Hz; 7.13 ppm, 1H, t, J=7.3 Hz; 6.98 ppm, 1H, d, J=7.3 Hz; 6.89 ppm, 1H, t, J=54.3 Hz; 3.91 ppm, 3H, s; 3.79 ppm, 1H, s; 3.25 ppm, 1H, s; 3.13 ppm, 1H, s; 2.67 ppm, 1H, bs; 2.67 ppm, 1H, bs; 2.17-2.09 ppm, 2H, m; 1.22 ppm, 1H, t, J=8.1 Hz; 1.16 ppm, 1H, t, J=8.1 Hz.

Step f): Preparation of the Compound of Formula IX:

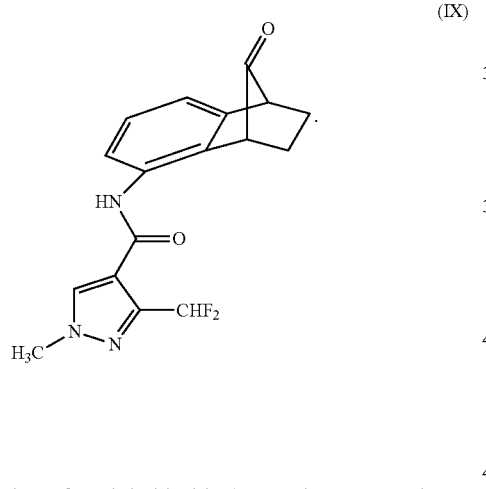

(IX)

To a solution of oxalyl chloride (0.41 ml, 4.87 mmol, 6.1 eq) in dichloromethane (4 ml) at −60° C. is added a solution of dimethyl sulfoxide (0.69 ml, 9.74 mmol, 12.2 mmol) in dichloromethane (1.3 ml). After five minutes spent stirring at the same temperature, a solution of 3-difluoromethyl-1-methyl-1H-pyrazole-4-carboxylic acid (9-hydroxy-1,2,3,4-tetrahydro-1,4-methano-naphthalen-5-yl)-amide (266 mg, 0.8 mmol, 1 eq) in dichloromethane (1.3 ml) is added dropwise. The resulting mixture is stirred fifteen minutes at −60° C. before the slow addition of a solution of triethylamine (3.1 ml, 22.2 mmol, 27.8 eq) in dichloromethane (1.3 ml). The reaction is stirred five more minutes at this temperature before it is allowed to warm up to 25° C. It is then diluted with ethyl acetate and poured on water. After separation of the layers, the aqueous phase is extracted twice with ethyl acetate, the combined organic extracts are washed twice with a saturated aqueous sodium bicarbonate solution, before being dried over solid sodium sulphate, filtered and concentrated under vacuum. The residue is purified by chromatography column (silica gel, elution with dichloromethane:methanol 39:1). 208 mg of the title compound are obtained (79% Yield).

Step g): Preparation of the Compound of Formula I

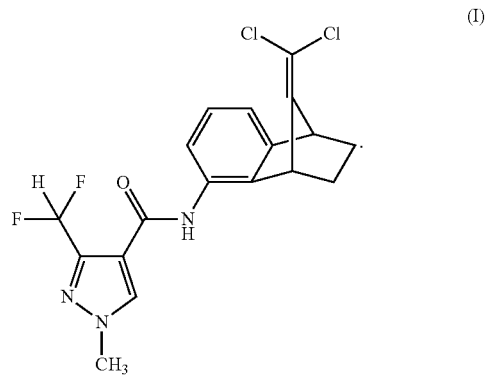 [SMILES: Cn1cc(C(=O)Nc2cccc3c2C2CCC3C2=C(Cl)Cl)c(C(F)F)n1]

(I)

A suspension of the compound of formula IX (400 mg, 1.2 mmol) and triphenylphosphane (2.7 mmol, 2.2 eq) in acetonitrile (2.5 ml) was stirred at ambient temperature. Carbon tetrachloride (290 μl, 1.8 mmol, 1.5 eq) was then added dropwise over 5 minutes. The reaction mixture was then stirred at 60° C. and quickly became a deep orange solution. After 6 hours the reaction was stopped and cooled to ambient temperature (adjudged complete via GCMS). The chemical yield of the compound of formula I in this step was calculated as 76%.

What is claimed is:

1. A process for the preparation of the compound of formula I

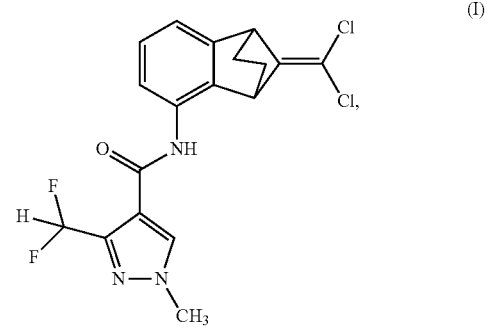 [SMILES: Cn1cc(C(=O)Nc2cccc3c2C2CCC3C2=C(Cl)Cl)c(C(F)F)n1]

(I)

which process comprises
a) reacting the compound of formula II

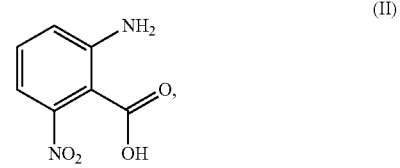 [SMILES: Nc1cccc([N+](=O)[O-])c1C(=O)O]

(II)

with cyclopentadiene in the presence of an alkylnitrite and an inert solvent to a compound of formula III

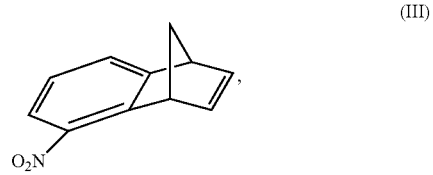 [SMILES: O=[N+]([O-])c1cccc2c1C1C=CC2C1]

(III)

b) reacting the compound of formula III in the presence of an oxidant and an inert solvent to the compound of formula IV

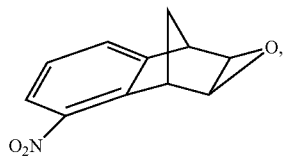
(IV)

c) hydrogenating the compound of formula IV in the presence of a metal catalyst and an inert solvent under hydrogen atmosphere to the compound of formula V

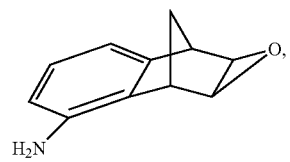
(V)

d) reacting the compound of formula V in the presence of a Brönsted acid followed by a reducing agent to the compound of formula VI

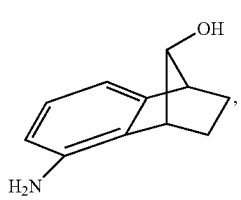
(VI)

e) reacting the compound of formula VI with a compound of formula VII

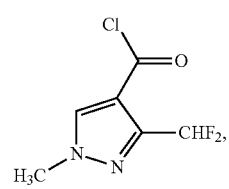
(VII)

in the presence of a base to a compound of formula VIII

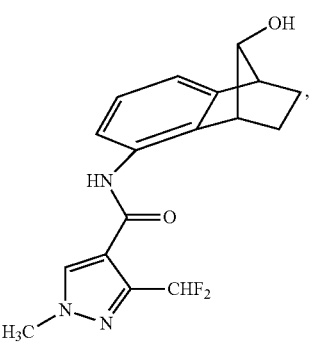
(VIII)

f) converting the compound of formula VIII in the presence of an oxidising agent to the compound of formula IX

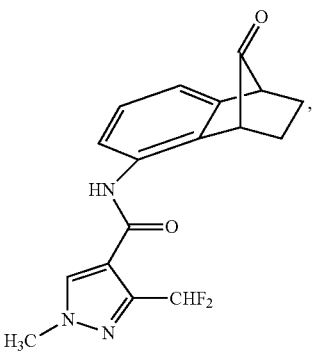
(IX)

and g) reacting the compound of formula IX in the presence of triphenylphosphane/carbon tetrachloride or triphenylphosphane/bromotrichloromethane to the compound of formula I.

2. A process according to claim 1, wherein in step a) tert-butylnitrite is used as the alkylnitrite.

3. A process according to claim 1, wherein in step b) meta-chloro-perbenzoic acid is used as the oxidant.

4. A process according to claim 1, wherein in step c) rhodium on carbon is used as the metal catalyst.

5. A process according to claim 1, wherein in step d) hydrobromic acid in water is used as Brönsted acid and a combination of activated zinc and acetic acid is used as reducing agent.

6. A process according to claim 1, wherein step g) is performed in the presence of triphenylphosphane/carbon tetrachloride.

7. A process according to claim 1, wherein
in step a) tert-butylnitrite is used as the alkylnitrite;
in step b) meta-chloro-perbenzoic acid is used as the oxidant;
in step c) rhodium on carbon is used as the metal catalyst;
in step d) hydrobromic acid in water is used as Brönsted acid and a combination of activated zinc and acetic acid is used as reducing agent;
and step g) is performed in the presence of triphenylphosphane/carbontetrachloride.

8. The compound of formula IV

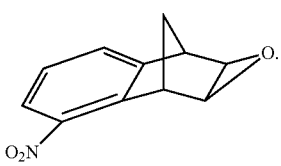
(IV)

9. The compound of formula V
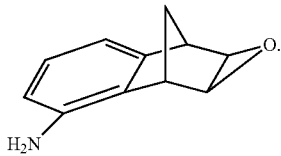
(V)
10. The compound of formula VI
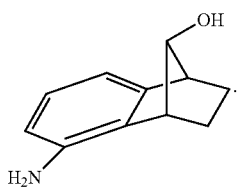
(VI)
11. The compound of formula VIII
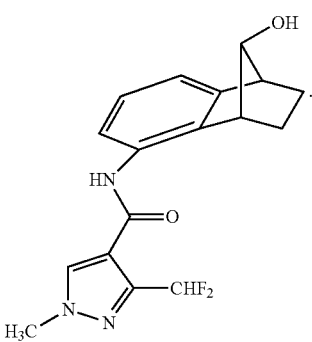
(VIII)
* * * * *